United States Patent [19]
Beebe et al.

[11] Patent Number: 5,630,527
[45] Date of Patent: May 20, 1997

[54] ELECTRONICALLY CONTROLLED, POSITIVE-DISPLACEMENT FLUID DISPENSER

[75] Inventors: W. Scott Beebe, Ashland; Michael J. Leuschner, Millville, both of Mass.

[73] Assignee: Philip Fishman Corporation, Hopkinton, Mass.

[21] Appl. No.: 304,267

[22] Filed: Sep. 12, 1994

[51] Int. Cl.⁶ .................................................. B67B 7/00
[52] U.S. Cl. ............................ 222/1; 222/63; 222/333; 222/390
[58] Field of Search ........................... 222/1, 63, 137, 222/325–327, 333, 390; 604/155, 224

[56] References Cited

U.S. PATENT DOCUMENTS

| | | | |
|---|---|---|---|
| 4,598,840 | 7/1986 | Burg | 222/135 |
| 4,634,431 | 1/1987 | Whitney et al. | 222/333 X |
| 4,848,606 | 7/1989 | Taguchi et al. | 222/333 |
| 4,950,134 | 8/1990 | Bailey et al. | |
| 5,219,099 | 6/1993 | Spence et al. | 222/325 |
| 5,348,585 | 9/1994 | Weston | 222/63 X |

*Primary Examiner*—Gregory L. Huson
*Attorney, Agent, or Firm*—Timothy J. Shea, II

[57] ABSTRACT

A fluid dispenser system, and method of use thereof primarily in industrial applications requiring the dispensing of fluids such as epoxies, silicones, adhesives, etc., allowing for very precise control of the volume of fluid extruded. The system comprises an ergonomic, handheld applicator accommodating a conventional medical syringe, wherein the ergonomic, handheld applicator is attached by a power cord to an electronic control unit. The applicator is provided with a stepping motor that drives a piston or screw a specific distance in response to an electronic signal generated by the control unit. Displacement of the piston or screw creates a positive pressure on a fluid contained in the syringe, thereby causing fluid extrusion from the syringe.

8 Claims, 4 Drawing Sheets

ELECTRONICALLY CONTROLLED, POSITIVE-DISPLACEMENT FLUID DISPENSER

FIELD OF THE INVENTION

The present invention relates to a fluid dispenser system and method of use thereof, primarily in industrial applications requiring the dispensing of fluids such as epoxies, silicones, adhesives, etc., although other applications, such as use in dentistry and the food service industry, are certainly anticipated.

BACKGROUND OF THE INVENTION

Dispensing consistent, controllable, measured amounts of fluids such as adhesives, epoxies, lubricants, etc. at an assembly plant workstation is a long-standing problem facing manufacturers concerned with precision product assembly and business efficiency. As can be imagined, it is imperative that the optimum amount of fluid be dispensed if a quality good is to be produced. If too little fluid is dispensed, the product might be unsafe to use as designed. If too much fluid is dispensed, the product might be unsightly, messy, or unsafe; further, wasted fluid results in significant cost inefficiencies.

One solution to this problem is to provide a handheld applicator having a reservoir of fluid and attached to a source of the driving force needed to extrude the fluid. Use of a medical syringe as a reservoir and of a pressure-driven piston to provide the driving force on the fluid to be extruded are known in the art. The extant devices most similar to this invention are the syringe pump and the pneumatic pressure-driven fluid dispenser.

A syringe pump is a medical device that continuously introduces a fluid into an intravenous tube. These devices usually employ a gravity-fed tube attached to a reservoir (usually an intravenous bag or bottle) and a motor-driven pump that regulates the flow of fluid via a cam that alternately compresses and releases the tube.

A pneumatic pressure-driven fluid dispenser has a medical syringe used to store and apply the fluid to be dispensed attached to a control unit, which control unit in turn is attached to a compressed air supply (usually "shop air"). Fluid is dispensed when a controlled burst of pneumatic pressure depresses the syringe plunger a specific distance. However, neither of these devices reads on the presently claimed invention.

A major drawback of these conventional dispensers designed to extrude a precise volume of a fluid, such as industrial adhesives and the like, is that the "dosage" of fluid to be extruded cannot be controlled as precisely as desired.

In addition to enabling precise volumetric control, the ideal fluid dispenser should be an unobtrusive component in an assembly line workstation. It should conveniently be in reach of the worker, yet not impede the assembly process. Further, because of the significant physical and economic costs associated with repetitive motion syndrome (a.k.a. "carpal tunnel syndrome"), it is desirable that the fluid dispenser have an ergonomic design to minimize the incidence in assembly workers of injuries due to this syndrome.

The present invention provides an elegant solution to all of these problems.

SUMMARY OF THE INVENTION

The present invention is a fluid dispenser system, and method of use thereof primarily in industrial applications requiring the dispensing of fluids such as epoxies, silicones, adhesives, etc., allowing for very precise control of the volume of fluid extruded. The system comprises an ergonomic, handheld applicator capable of accommodating a conventional syringe and piston assembly, wherein the ergonomic, handheld applicator is attached by a control tether to an electronic control unit. The applicator is provided with a stepping motor that displaces a drive rod a specific distance in response to an electronic signal generated by the control unit. Displacement of the drive rod creates a positive pressure on a fluid contained in the syringe, thereby causing fluid extrusion from the syringe. As can be expected, because the drive rod is displaced a precise distance, this system allows for very precise control of the volume of fluid extruded.

Prior to this invention, only approximate volumes of fluid were able reliably to be extruded from a handheld applicator. In addition to potentially dispensing either too much or too little fluid, such dispensers were difficult to control and very inefficient delivery systems. A further problem is the relatively high incidence of repetitive motion syndrome among those using prior known devices.

The significance of the present invention is that it enables a precise and optimum amount of fluid to be dispensed in a manner that results in greater cost efficiency and reduces the incidence of worker injury due to repetitive motion syndrome.

Accordingly, an object of the present invention is to provide a means for dispensing an optimum amount of fluid. Another object of the present invention is to provide such a dispensing means that does not pose a significant risk of injury due to repetitive motion syndrome. Further objects and advantages of the invention will become apparent from the description of the drawings and the invention, which follow.

DESCRIPTION OF THE PREFERRED EMBODIMENTS

Figure 1:
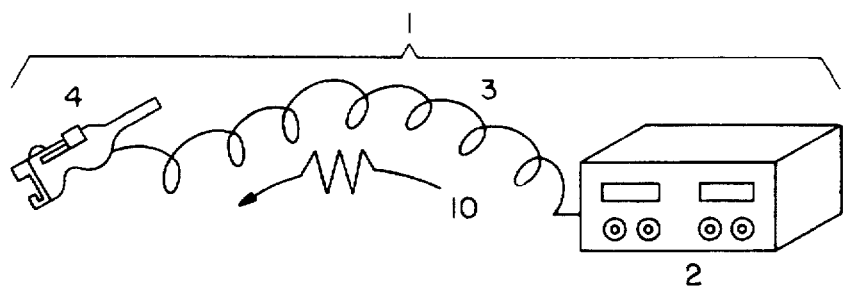
FIG. 1 is a schematic diagram of one embodiment of the electronically controlled, positive-displacement fluid dispenser system presently claimed.
Figure 2:
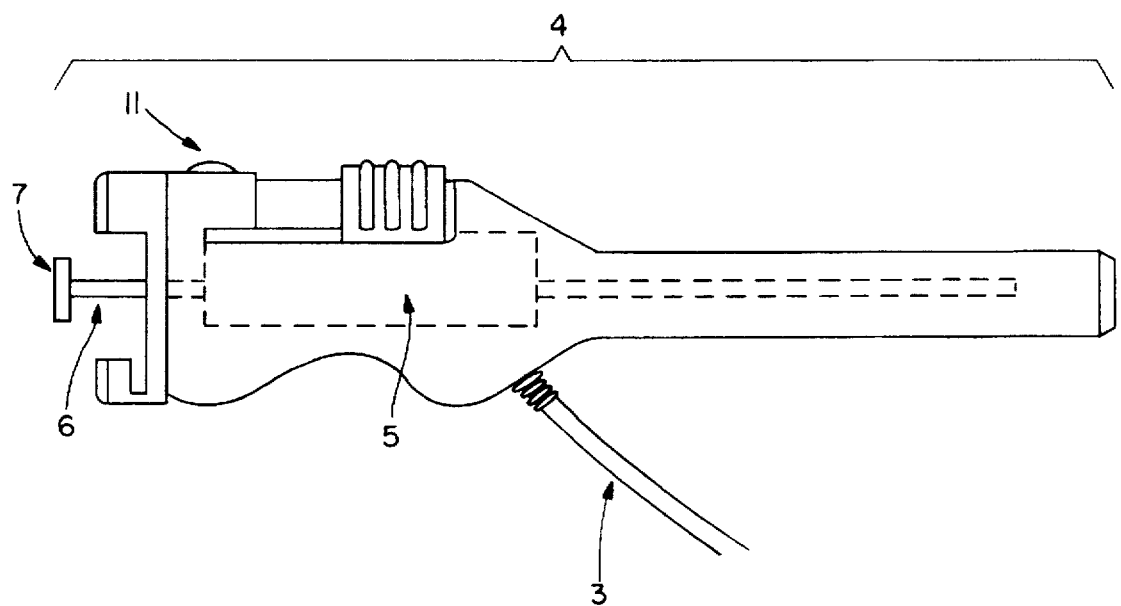
FIG. 2 shows a side view of one configuration of the ergonomically designed handheld applicator of the present invention.
Figure 3:
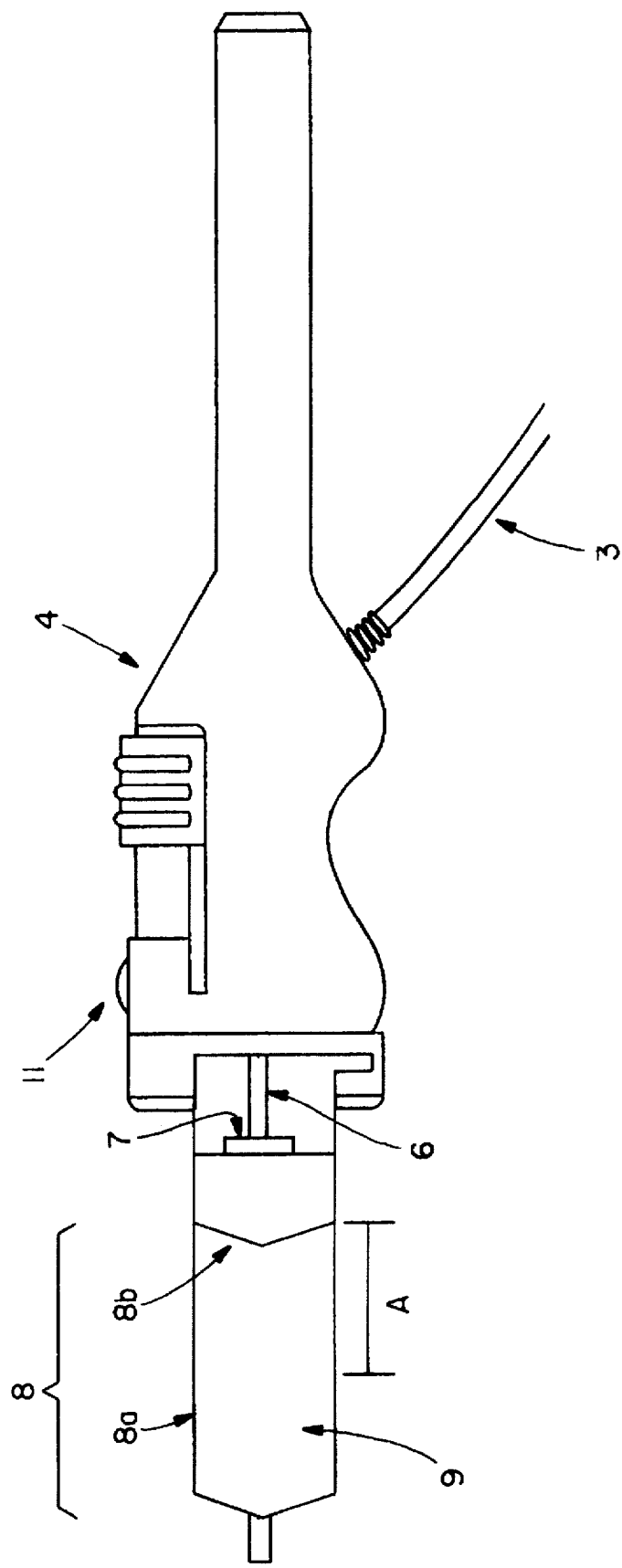
FIG. 3 shows the ergonomically designed handheld applicator of FIG. 2 in combination with a conventional syringe and piston assembly.

An electronically controlled, positive-displacement fluid dispenser system is provided. The dispenser is primarily constructed of elements made from durable, lightweight materials. As shown in FIGS. 1, 2, and 3, the dispenser system 1 comprises a control unit 2 attached by a control tether 3 to an ergonomically designed handheld applicator 4. The control tether may be advantageously positioned on the handheld applicator so as to minimize both interference with the assembly operation and also stress on the operator's wrist and arm.

The handheld applicator 4 is provided with a stepping motor 5 engagable with a drive rod 6. Drive rod 6 inserts into a conventional syringe (8a) and piston (8b) assembly 8 for storage and application of the fluid 9 to be dispensed. Drive rod 6 is designed to engage with piston 8b in the conventional syringe and piston assembly 8. Drive rod 6 optionally may be attached to a load distribution plate 7 which articulates with piston 8b.

The control unit may allow the dispenser operator to select either pre-programmed fluid volumes and flowrates or a variable volume and flowrate, as required. When the operator depresses finger switch 11, an electronic drive signal 10 is generated by the control unit 2 and transmitted via control tether 3 to the stepping motor 5. Stepping motor 5 then displaces drive rod 6, and optionally load distribution plate 7, a specific variable distance A and extruding the precise volume of fluid 9 desired.

In this embodiment, once the drive rod has been displaced the specified distance—and the desired, metered volume of fluid is extruded—the control unit interrupts the power supply sent to the applicator via the tether. Thus, by regulating the power supplied to the stepping motor, the volume of fluid dispensed is controlled. However, if the operator elects manual control, fluid extrusion is controlled by the operator via the finger switch. Fluid will then be extruded at the selected flowrate for as long as the finger switch is depressed.

Figure 4:
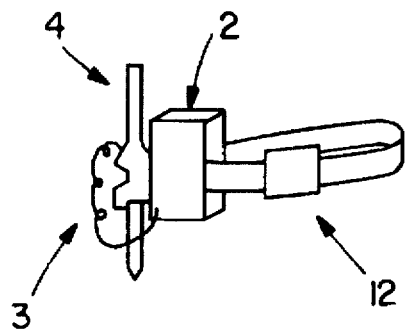
FIG. 4 shows an embodiment of the invention wherein the control unit has an internal power supply, thereby allowing for portable operation.
Figure 5:
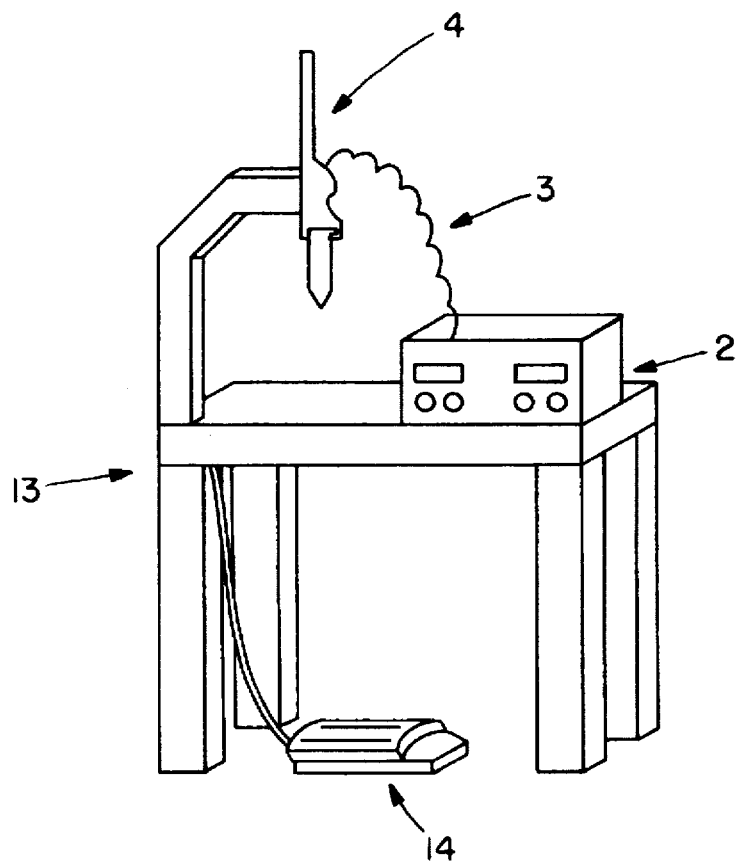
FIG. 5 shows the fluid dispenser system of the present invention stand-mounted and controlled via a footpedal.
Figure 6:
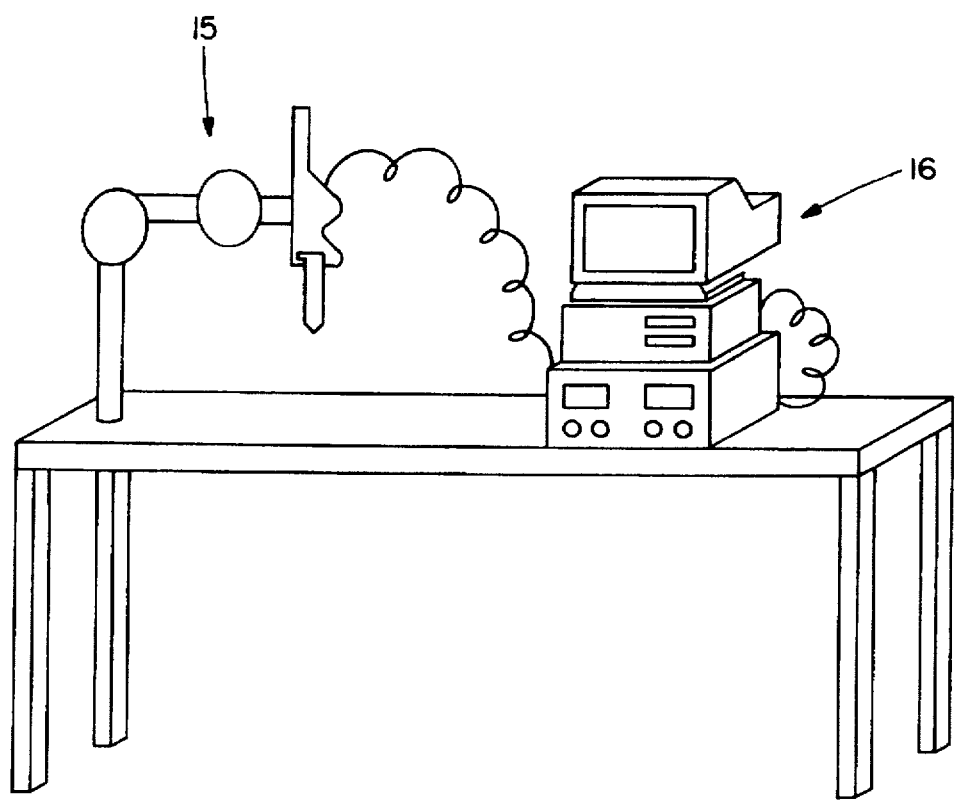
FIG. 6 shows the fluid dispenser system of the present invention integrated into an XYZ table, wherein the control unit receives input from a microprocessor.
Figure 7:
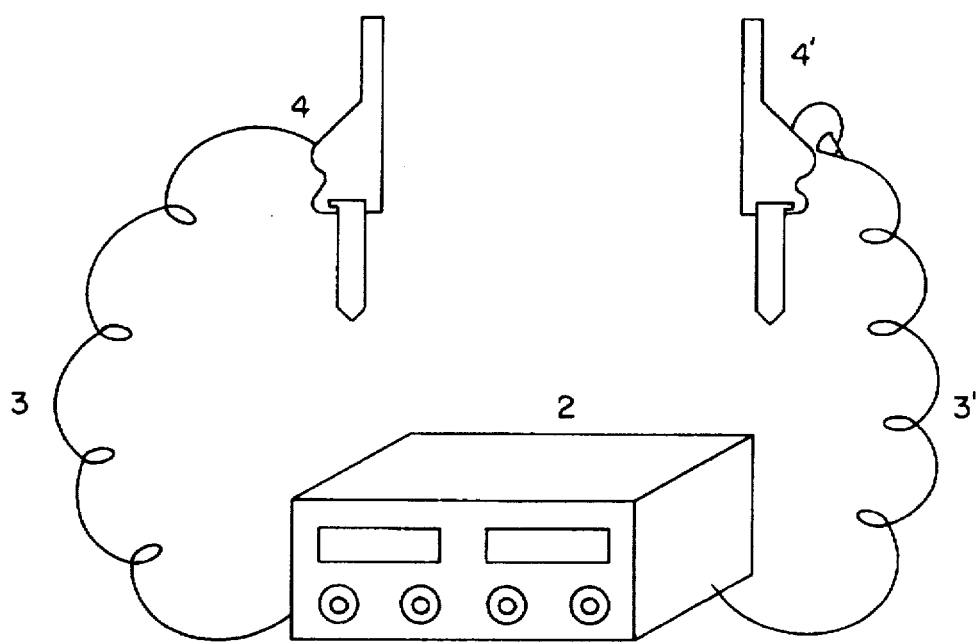
FIG. 7 shows an embodiment of the present invention wherein the control unit simultaneously controls two handheld applicators.

A further embodiment is shown in FIG. 4, wherein the control unit has an internal power supply, thereby allowing for portable operation. In this embodiment, the entire dispenser system could be worn as a belt pack 12. An additional embodiment is shown in FIG. 5, wherein the dispenser system is mounted to a stand 13 and controlled via a footpedal 14. An even further embodiment of the present invention is shown in FIG. 6 wherein the fluid dispenser system of the present invention integrated into an XYZ table 15, wherein the control unit receives personal computer 16. One further embodiment is shown in FIG. 7, wherein control unit 2 simultaneously controls two handheld applicators 4 and 4' via control tethers 3 and 3'.

It is understood that each of these embodiments allows for the use by control unit Z of either a self-contained power source or a power cord that may draw power either from a storage device or from a step-down transformer (to convert household current to current appropriate to drive the stepping motor).

The invention may be embodied in other specified forms without departing from the spirit or essential characteristics thereof. The present embodiments are therefore to be considered in all respects as illustrative and not restrictive, and all changes which come within the meaning and range or equivalency of the claims are therefore intended to be embraced therein.

What is claimed is:

1. An electronically controlled, positive-displacement fluid dispenser system comprising an electronic control unit capable of allowing the use of either preprogrammed settings or variable settings, a control tether, and an ergonomic, handheld applicator having a finger switch, wherein the ergonomic, handheld applicator is attached to the electronic control unit by the control tether and wherein the ergonomic, handheld applicator is capable of accommodating a conventional syringe and piston assembly and wherein the ergonomic, handheld applicator is provided with a motor that displaces a drive rod, to be disposed within said conventional syringe and piston assembly, a specific distance in response to an electronic drive signal generated by the control unit after the finger switch is depressed by the operator.

2. The electronically controlled, positive-displacement fluid dispenser system, as claimed in claim 1, wherein the electronic control unit has a self-contained power source.

3. The electronically controlled, positive-displacement fluid dispenser system, as claimed in claim 1, wherein the electronic control unit has a power cord that may draw power either from a storage device or from a step-down transformer to convert household current to current appropriate to drive the stepping motor.

4. The electronically controlled, positive-displacement fluid dispenser system, as claimed in claim 1, wherein the drive rod is attached to a load distribution plate, which engages the piston in the conventional syringe and piston assembly.

5. A method of extruding a precise volume of fluid from an electronically controlled, positive-displacement fluid dispenser system comprising an electronic control unit capable of allowing the use of either preprogrammed settings or variable settings, a control tether, and an ergonomic, handheld applicator having a finger switch, wherein the ergonomic, handheld applicator is attached to the electronic control unit by the control tether and wherein the ergonomic, handheld applicator is capable of accommodating a conventional syringe and piston assembly and wherein the ergonomic, handheld applicator is provided with a motor that displaces a drive rod, to be disposed within said conventional syringe and piston assembly, a specific distance in response to an electronic drive signal generated by the control unit after the finger switch is depressed, which method comprises the steps of:

a) selecting on the control unit the desired volume of fluid to be extruded;

b) positioning the ergonomic, handheld applicator so as to advantageously apply the fluid extruded;

c) depressing the finger switch on the ergonomic, handheld applicator to generate electronic drive signal from the control unit to the motor that will drive the piston a specified distance in order to extrude precisely the volume of fluid desired;

wherein displacement of the drive rod engaged with the piston in the conventional syringe and piston assembly creates a positive pressure on the fluid contained in the syringe, thereby causing the extrusion of a precise volume of the fluid from the syringe.

6. The method of extruding a precise volume of fluid from an electronically controlled, positive-displacement fluid dispenser system, as claimed in claim 5, wherein the electronic control unit has a self-contained power source.

7. The method of extruding a precise volume of fluid from an electronically controlled, positive-displacement fluid dispenser system, as claimed in claim 5, wherein the electronic control unit has a power cord that may draw power either from a storage device or from a step-down transformer to convert household current to current appropriate to drive the stepping motor.

8. The method of extruding a precise volume of fluid from an electronically controlled, positive-displacement fluid dispenser system, as claimed in claim 5, wherein the drive rod is attached to a load distribution plate, which engages the piston in the conventional syringe and piston assembly.

* * * * *

UNITED STATES PATENT AND TRADEMARK OFFICE
CERTIFICATE OF CORRECTION

PATENT NO. : 5,630,527
DATED : May 20, 1997
INVENTOR(S) : W. Scott Beebe, et. al.

It is certified that error appears in the above-indentified patent and that said Letters Patent is hereby corrected as shown below:

Col. 3, line 42, after "receives" insert --input from a--.

Signed and Sealed this

Twenty-sixth Day of August, 1997

Attest:

BRUCE LEHMAN

Attesting Officer

Commissioner of Patents and Trademarks